(12) United States Patent
Wallenstein (10) Patent No.: US 9,095,378 B2
(45) Date of Patent: Aug. 4, 2015

(54) SPINAL STABILIZATION SYSTEM

(71) Applicant: K2M, Inc., Leesburg, VA (US)

(72) Inventor: Todd Wallenstein, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 169 days.

(21) Appl. No.: 13/675,175

(22) Filed: Nov. 13, 2012

(65) Prior Publication Data
US 2014/0135841 A1 May 15, 2014

(51) Int. Cl.
*A61B 17/70* (2006.01)
*A61B 17/88* (2006.01)

(52) U.S. Cl.
CPC ........... *A61B 17/7007* (2013.01); *A61B 17/701* (2013.01); *A61B 17/8863* (2013.01); *A61B 17/7032* (2013.01)

(58) Field of Classification Search
CPC .. A61B 17/70; A61B 17/7007; A61B 17/701; A61B 17/7032; A61B 17/8863
USPC .......... 606/246, 264–270, 279, 301, 305, 308
See application file for complete search history.

(56) References Cited

U.S. PATENT DOCUMENTS

| | | | |
|---|---|---|---|
| 5,113,685 A | 5/1992 | Asher et al. |
| 5,217,497 A | 6/1993 | Mehdian |
| 5,261,912 A | 11/1993 | Frigg |
| 5,658,286 A | 8/1997 | Sava |
| 5,667,508 A | 9/1997 | Errico et al. |
| 5,899,904 A | 5/1999 | Errico et al. |
| 5,910,142 A | 6/1999 | Tatar |
| 5,947,969 A | 9/1999 | Errico et al. |
| 6,102,912 A | 8/2000 | Cazin et al. |
| 6,451,021 B1 | 9/2002 | Ralph et al. |
| 6,482,207 B1 | 11/2002 | Errico |
| 6,540,749 B2 | 4/2003 | Schafer et al. |
| 6,582,434 B2 | 6/2003 | Kawakami et al. |
| 6,644,087 B1 | 11/2003 | Ralph et al. |
| 7,503,918 B2 | 3/2009 | Baccelli et al. |
| 7,520,879 B2 | 4/2009 | Justis et al. |
| 7,563,274 B2 | 7/2009 | Justis et al. |
| 7,569,061 B2 | 8/2009 | Colleran |
| 7,588,575 B2 | 9/2009 | Colleran et al. |
| 7,588,588 B2 | 9/2009 | Spitler et al. |
| 7,604,653 B2 | 10/2009 | Kitchen |
| 7,618,442 B2 | 11/2009 | Spitler et al. |
| 7,766,942 B2 | 8/2010 | Patterson et al. |
| 7,931,676 B2 | 4/2011 | Veldman et al. |
| 2002/0161368 A1 | 10/2002 | Foley et al. |
| 2005/0065515 A1 | 3/2005 | Jahng |
| 2008/0027432 A1 | 1/2008 | Strauss et al. |
| 2008/0086130 A1 | 4/2008 | Lake et al. |
| 2008/0262546 A1 | 10/2008 | Calvosa et al. |
| 2009/0018593 A1 | 1/2009 | Barrus et al. |
| 2011/0087298 A1 | 4/2011 | Jones |
| 2011/0190823 A1 | 8/2011 | Bergeron et al. |

*Primary Examiner* — Eduardo C Robert
*Assistant Examiner* — David Comstock
(74) *Attorney, Agent, or Firm* — Carter, DeLuca, Farrell & Schmidt, LLP

(57) ABSTRACT

A spinal stabilization system includes a connecting rod and a bone screw. The connecting rod includes an elongate rounded section, a pair of elongate rail portions, and a pair of neck portions connecting the elongate rounded section with the respective pair of elongate rail portions. Each elongate rail portion extends radially outward from the elongate rounded section and is diametrically opposed to the other elongate rail portion. The bone screw includes a head portion defining a slot, a shank extending longitudinally from the head portion, and a set screw configured to secure the connecting rod in the slot. The slot includes a leading end portion configured to receive one of the pair of elongate rail portions and a trailing end portion configured to engage the set screw, wherein the connecting rod is pivotable about the elongate rounded section in the slot.

16 Claims, 5 Drawing Sheets

SPINAL STABILIZATION SYSTEM

BACKGROUND

1. Technical Field

The present disclosure relates to orthopedic surgical devices and, more particularly, to a spinal stabilization system and a method of use therefor.

2. Background of Related Art

The spinal column is a complex system of bones and connective tissues that provide support for the human body and protection for the spinal cord and nerves. The adult spine is comprised of an upper and lower portion. The upper portion contains twenty-four discrete bones, which are subdivided into three areas including seven cervical vertebrae, twelve thoracic vertebrae, and five lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury, which restrict the range of motion of the spine or interfere with important elements of the nervous system. The problems include, for example, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages and cadaver and human bone implants. In order to facilitate stabilizing the spine and keeping the interbody in position, other implants are commonly employed, such as bone screws and connecting rods. Depending on the pathology and treatment, a surgeon will select the appropriate spinal rod material and size, specifically, the cross-sectional diameter.

To meet the problem of providing a rigid pedicle screw and rod construct, especially for addressing the demands of stiff deformity corrections, larger rod constructs have been made to improve the strength of the screw and rod construct. Spinal rods are typically made of a titanium alloy. However when large deformity corrections need to be made, these rods are not always strong enough. Larger diameter stainless steel rods have been made for these applications, but a larger rod requires a larger mating screw head to contain the rod which in turn increases the profile of the construct. In addition, in order to reduce the likelihood of material incompatibility in vivo, the screw assembly also needs to be made of stainless steel to match the rod material, which is not a cost effective alternative.

Therefore, a need exists for a cost effective, rigid screw and rod construct that can still maintain a low profile, while maintaining the surgical correction.

SUMMARY

In accordance with an embodiment of the present disclosure, there is provided a spinal stabilization system including a connecting rod and a bone screw. The connecting rod includes an elongate rounded section, a pair of elongate rail portions, and a pair of neck portions connecting the elongate rounded section with the respective pair of elongate rail portions. Each elongate rail portion extends radially outward from the elongate rounded section and diametrically opposes the other rail portion. The bone screw includes a head portion defining a slot, a shank extending longitudinally from the head portion, and a set screw configured to secure the connecting rod in the slot. The slot includes a leading end portion configured to receive one of the pair of elongate rail portions and a trailing end portion configured to engage the set screw, wherein the connecting rod is pivotable about the elongate rounded section in the slot.

In another embodiment, at least one of the pair of elongate rail portions may include a non-circular cross-section. In particular, the non-circular cross-section may be rectangular. The elongate rounded section may have a substantially circular cross-section. In addition, at least one of the pair of elongate rail portions may include an arcuate surface. Furthermore, the arcuate surface of the at least one of the elongate rail portions may conform to a contour of the leading end portion of the slot defined in the bone screw. Alternatively, at least one of the pair of elongate rail portions may include a planar surface configured to be in a surface contact with the set screw.

In still another embodiment, the width of at least one of the pair of elongate rail portions may be smaller than the diameter of the elongate rounded section. In addition, the neck portion of the connecting rod may be narrower than the elongate rounded section of the connecting rod. Each neck portion may include a pair of concave sides joining the elongate rail portion with the elongate rounded section.

In yet another embodiment, the connecting rod may be monolithically formed. Additionally, the connecting rod may be made of titanium or titanium alloy. The bone screw and the connecting rod may be made of the same material.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein.

DETAILED DESCRIPTION OF EMBODIMENTS

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

Figure 1:
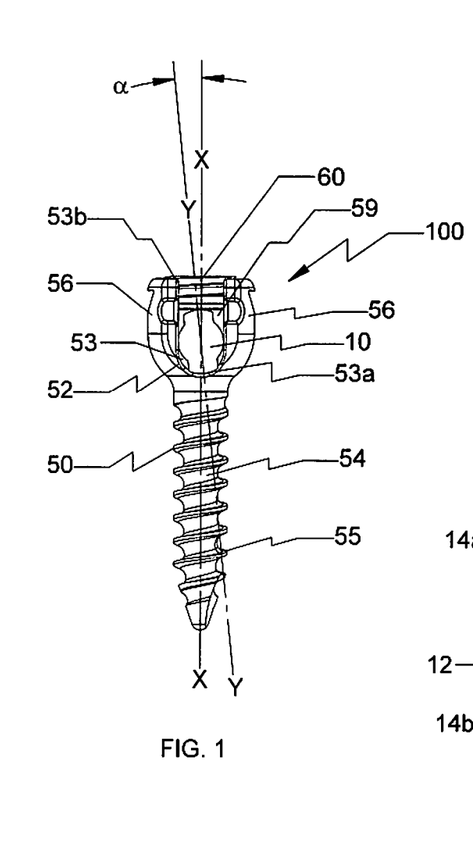
FIG. 1 is a front view of a spinal stabilization system in accordance with an embodiment of the present disclosure.
Figure 2:
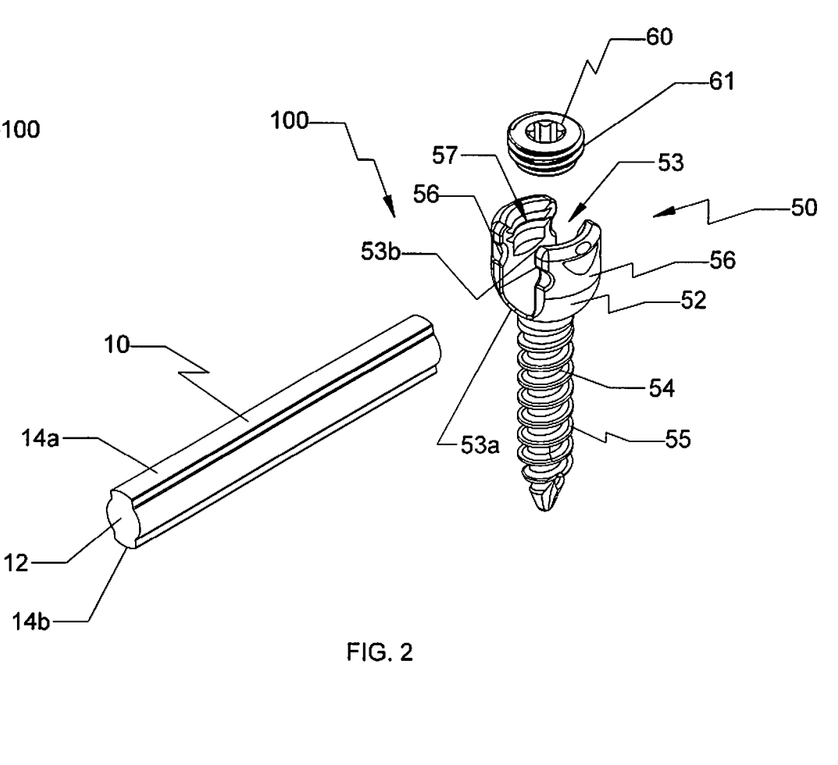
FIG. 2 is an exploded perspective view of the spinal stabilization system of FIG. 1 with parts separated.

With reference to FIGS. 1 and 2, an embodiment of the present disclosure is shown generally as a spinal stabilization system 100. Spinal stabilization system 100 includes at least one bone screw 50 and a connecting rod 10. Connecting rod 10 is configured and dimensioned to be selectively and releasably secured to bone screw 50. Connecting rod 10 is defined by an elongate body of a particular length. The elongate body is made of a biocompatible material such as Titanium (Ti—CP) and its alloys (e.g., Ti-6Al-4V), Cobalt-Chrome Alloy (CoCr), or Stainless Steel (SS).

Figure 3:
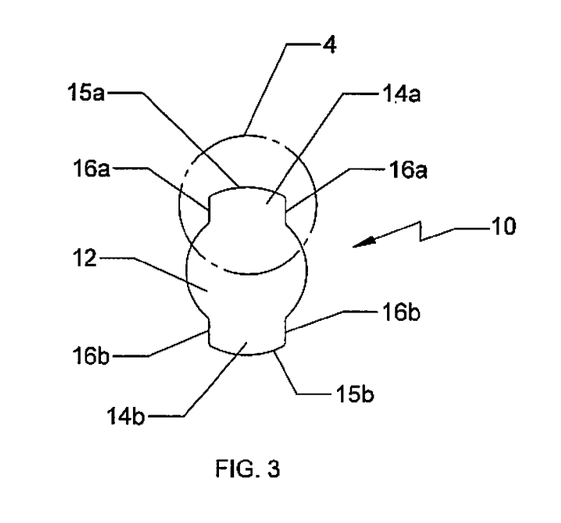
FIG. 3 is a front view of a connecting rod of the spinal stabilization system of FIG. 1.

With reference to FIGS. 2 and 3, the elongate body of connecting rod 10 includes an elongate rounded section 12 having a substantially circular cross-section, a pair of elongate rail portions 14a, 14b, and a pair of neck portions 16a, 16b that connect and transition elongate rounded section 12 into the respective elongate rail portions 14a, 14b, thereby providing reduced stress concentration along the elongate body of connecting rod 10. Neck portions 16a, 16b define a pair of concave sides joining elongate rail portions 14a, 14b to elongate rounded section 12.

Figure 4:
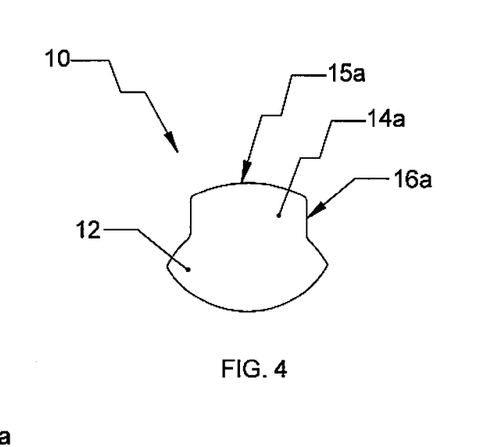
FIG. 4 is a front view of the area of detail indicated in FIG. 3.

With reference to FIGS. 3 and 4, each elongate rail portion 14a, 14b extends radially outward from elongate rounded section 12 and is diametrically opposed to the other rail portion. While the pair of elongate rail portions 14a, 14b of connector rod 10 extends radially outward from elongate rounded section 12, elongate rail portions 14a, 14b do not appreciably increase the height profile of the screw-rod combination. Connecting rod 10 is disposed entirely within slot 53 of bone screw 50. Connecting rod 10 affords greater strength and rigidity in comparison with ordinary circular rods with comparable dimensions. As such, connecting rod 10 and bone screw 50 construct affords greater rigidity and strength without significant increase in bulk and profile.

Moreover, the width of each elongate rail portion 14a, 14b is smaller than the diameter of elongate rounded section 12. Such a configuration facilitates pivoting of connecting rod 10 about elongate rounded section 12 within a slot 53 defined in a head portion 52 of bone screw 50, as will be described hereinbelow. The pair of elongate rail portions 14a, 14b is substantially identical to each other. As such, either one of the pair of elongate rail portions 14a, 14b may be placed in leading end portion 53a of slot 53. In addition, the pair of elongate rail portions 14a, 14b is adapted to be placed in contact with set screw 60.

With continued referenced to FIGS. 3 and 4, elongate rail portions 14a, 14b include arcuate surfaces 15a, 15b, respectively. At least one of arcuate surfaces 15a, 15b may conform to the contour of leading end portion 53a to facilitate pivoting of connecting rod 10 about elongate rounded section 12 when connecting rod 10 is partially secured within slot 53, i.e., prior to set screw 60 being fully tightened.

Moreover, such a configuration facilitates securement of connecting rod 10 within slot 53 at a desired orientation. When set screw 60 partially locks connecting rod 10 within slot 53, the surgeon may, e.g., pivot connecting rod 10 about elongate rounded section 12 to place connecting rod 10 in a desired orientation. However, an elongate rail portion defining, e.g., a planar surface, will tend to orient elongate rail portion towards a central orientation upon tightening of set screw 60. However, arcuate surfaces 15a, 15b being in contact with set screw 60 enables the surgeon to maintain the desired orientation of connecting rod 10 during tightening of set screw 60.

With particular reference to FIG. 3, each elongate rail portion 14a, 14b has a non-circular cross-section. As shown, each elongate rail portion 14a, 14b has a substantially rectangular cross-section having suitable dimensions of, for example, about 6 mm×about 1 mm (0.246 in.×0.039 in.). However, it is envisioned that elongate rail portions 14a, 14b may have a cross-section that is substantially square, elliptical or any other shape to add rigidity to elongate rounded section 12 of connecting rod 10.

With reference back to FIGS. 2 and 3, elongate rounded section 12 of connecting rod 10 is configured and dimensioned to be received in slot 53 defined in a head portion 52 of bone screw 50, as will be described in detail hereinbelow. Elongate rounded section 12, the pair of elongate rail portions 14a, 14b, and the pair of neck portions 16a, 16b of connecting rod 10 may be monolithically formed as a unitary construct. For example, connecting rod 10 may be machined from a single piece of bar stock.

With reference back to FIGS. 1 and 2, bone screw 50 includes a head portion 52 configured to receive connecting rod 10 therein, a shank 54 extending longitudinally from head portion 52, and a set screw 60 threadably coupled to head portion 52 to secure connecting rod 10 in a slot 53 defined in head portion 52. Head portion 52 of bone screw 50 includes a pair of radially opposing walls 56 defining slot 53 therebetween. Radially opposing walls 56 include internal threads 57 configured for engaging external threads 61 of set screw 60. Slot 53 defines a substantially U-shape channel configured and dimensioned to receive connecting rod 10. Slot 53 includes a leading end portion 53a and a trailing end portion 53b. In particular, leading end portion 53a has an arcuate configuration configured to accommodate one of the pair of elongate rail portions 14a, 14b of connecting rod 10. In particular, arcuate surfaces 15a, 15b (FIG. 3) of connecting rod 10 conform to the contour of leading end portion 53a of slot 53. The arcuate configurations of both leading end portion 53a and connecting rod 10 facilitate pivoting of connecting rod 10 about elongate rounded section 12 when connecting rod 10 is partially secured therein, i.e., prior to set screw 60 being fully tightened.

As discussed hereinabove, elongate rail portions 14a, 14b each have a smaller width than the diameter of elongate rounded section 12. In this manner, slot 53 provides a slight gap 59 (FIG. 1) between an inner surface of wall 56 and elongate rail portions 14a, 14b of connecting rod 10. Under such a configuration, when set screw 60 partially locks connecting rod 10 within slot 53, the surgeon may, e.g., pivot, connecting rod 10 about elongate rounded section 12 within slot 53 to place connecting rod 10 in a desired orientation. Arcuate surfaces 15a, 15b of elongate rail portion 14a, 14b enables the surgeon to achieve the desired orientation during tightening of set screw 60 without difficulty.

Specifically, since connecting rod 10 is pivotable within slot 53 when connecting rod 10 is partially locked within slot 53, connecting rod 10 can be secured to one of a plurality of angular orientations by fully locking connecting rod 10 within slot 53 by fully tightening set screw 60, whereby a longitudinal axis "Y-Y" (FIG. 1) defined by connecting rod 10 defines an acute angle α with a longitudinal axis "X-X" (FIG. 1) defined by bone screw 50. This allows the surgeon the flexibility of adjusting the orientation of the connecting rod 10 for the rod-screw construct where the angular relationship between the connecting rod 10 and a first bone screw 50 may be different from the angular relationship between the connecting rod 10 and a second bone screw 50.

With continued reference to FIGS. 2 and 3, shank 54 of bone screw 50 includes threads 55 to facilitate insertion into vertebral bodies or other bones. Bone screw 50 may be made of a biocompatible material such as Titanium (Ti—CP) and its alloys (e.g., Ti-6Al-4V), Cobalt-Chrome Alloy (CoCr), or Stainless Steel (SS). In particular, head portion 52 and shank 54 may be monolithically formed.

Figure 5:
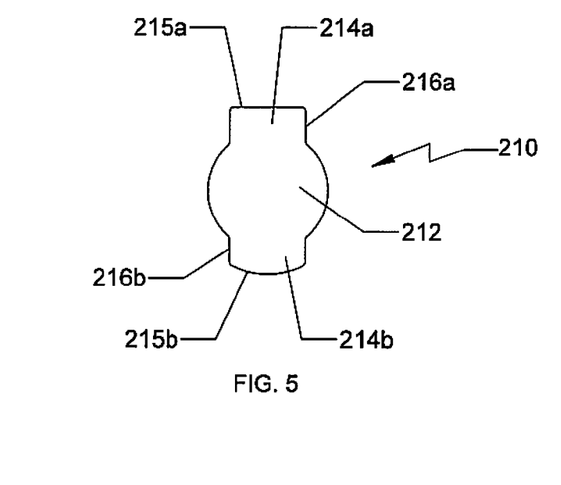
FIG. 5 is a front view of a connecting rod in accordance with another embodiment of the present disclosure.
Figure 6:
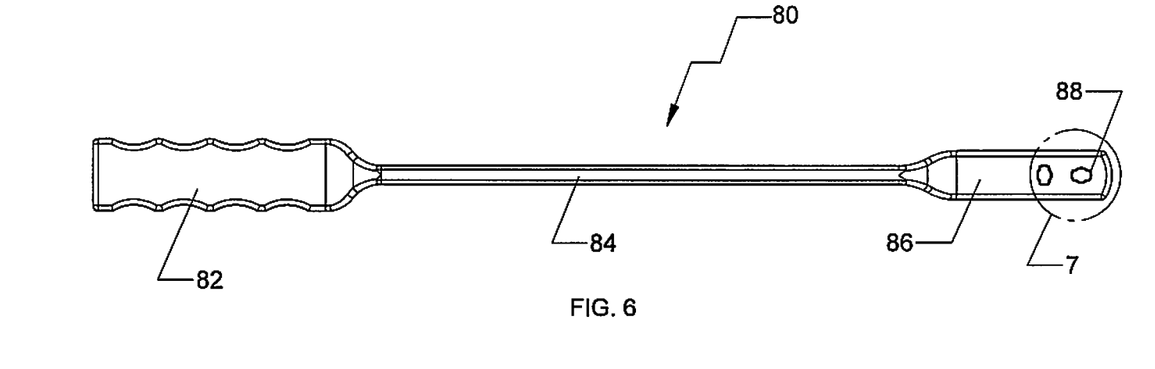
FIG. 6 is a side view of a rod bender device for use with the spinal stabilization system of FIG. 1.

With reference now to FIG. 5, there is provided a connecting rod 210 in accordance with another embodiment of the present disclosure. Connecting rod 210 may include an elongate body having an elongate rounded section 212 having a substantially circular cross-section, a pair of elongate rail portions 214a, 214b, and a pair of neck portions 216a, 216b that connect and transition elongate rounded section 12 into the respective elongate rail portions 14a, 14b, thereby providing reduced stress concentration along the elongate body of connecting rod 10. Each elongate rail portion 214a, 214b extends radially outward from elongate rounded section 212 and is diametrically opposed to the other rail portion.

However, in contrast to connecting rod 10, elongate rail portion 214a includes a planar surface 215a adapted to be in, e.g., a surface contact, with set screw 60. As discussed hereinabove, an elongate rail portion having a planar surface 215a will tend to orient elongate rail portion towards a central orientation upon tightening of set screw 60. Thus, connecting rod 210 may be utilized in surgical procedures in which it is desirable to orient connecting rod 210 to the central orientation upon tightening of set screw 60.

Moreover, trailing end portion 53b of slot 53 defines a substantially planar surface such that set screw 60 threadably inserted in slot 53 is substantially flush with trailing end portions 56b of the respective walls 56 when connecting rod 210 is positioned within slot 53 and secured by set screw 60 therein. However, elongate rail portion 214b may include an arcuate surface 215b to facilitate pivoting of connecting rod 210 within slot 53 of bone screw 50, as discussed hereinabove.

With reference now to FIGS. 6-9, spinal stabilization system 100 may further include rod bender devices 80. Each rod bender devices 80 define matching apertures 88 configured to receive and hold at least a portion of connecting rod 10 therein. Rod bender device 80 includes a handle member 82, an elongate body 84 extending distally from handle portion 82, and an engaging portion 86 coupled to elongate body 84. Elongate body 84 is coupled or formed with handle member 82 and engaging portion 86 so as to reduce stress concentration. Handle member 82 may contain scalloped sections to facilitate gripping by the user.

Engaging portion 86 defines at least one aperture 88 adapted and dimensioned to receive therethrough connecting rods 10, 210. In particular, inner walls that define aperture 88 are configured to permit insertion of connecting rod 10 through aperture 88 in a single orientation with respect to such aperture.

Figure 7:
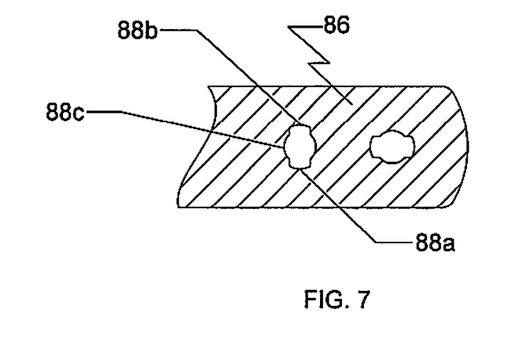
FIG. 7 is a side cross-sectional view of the area of detail indicated in FIG. 6.
Figure 8:
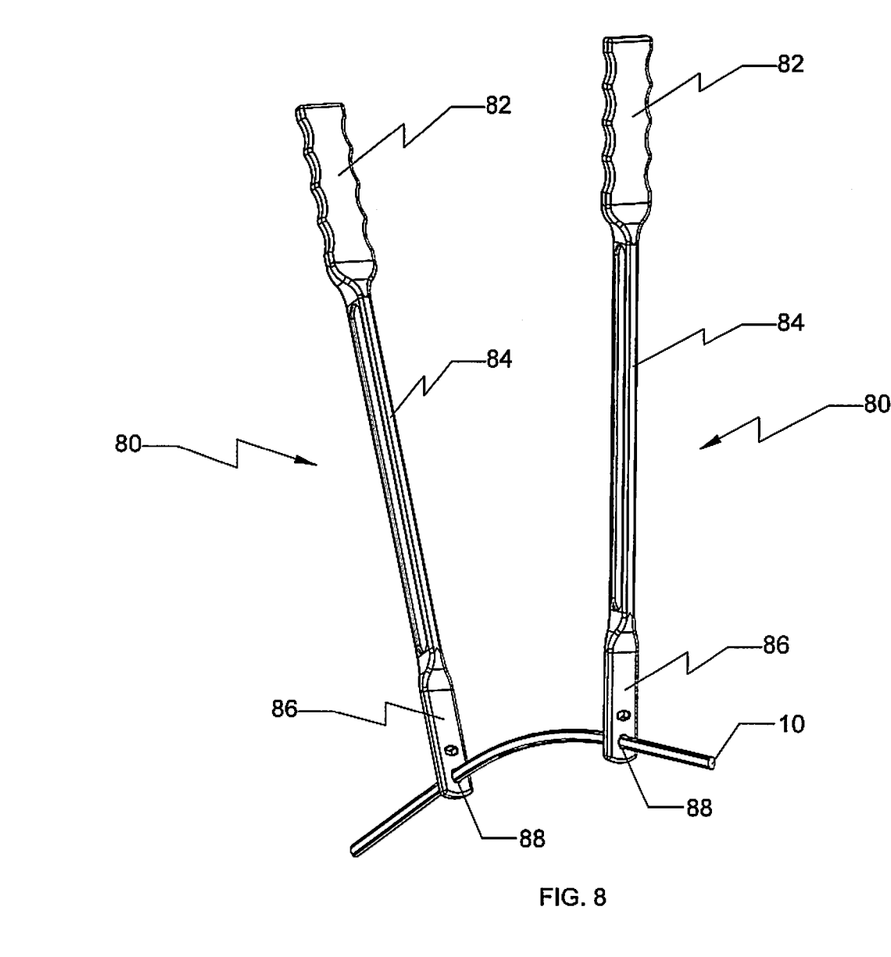
FIG. 8 is a perspective view of a pair of rod bender devices of FIG. 6 having the connecting rod of FIG. 3 inserted therethrough.
Figure 9:
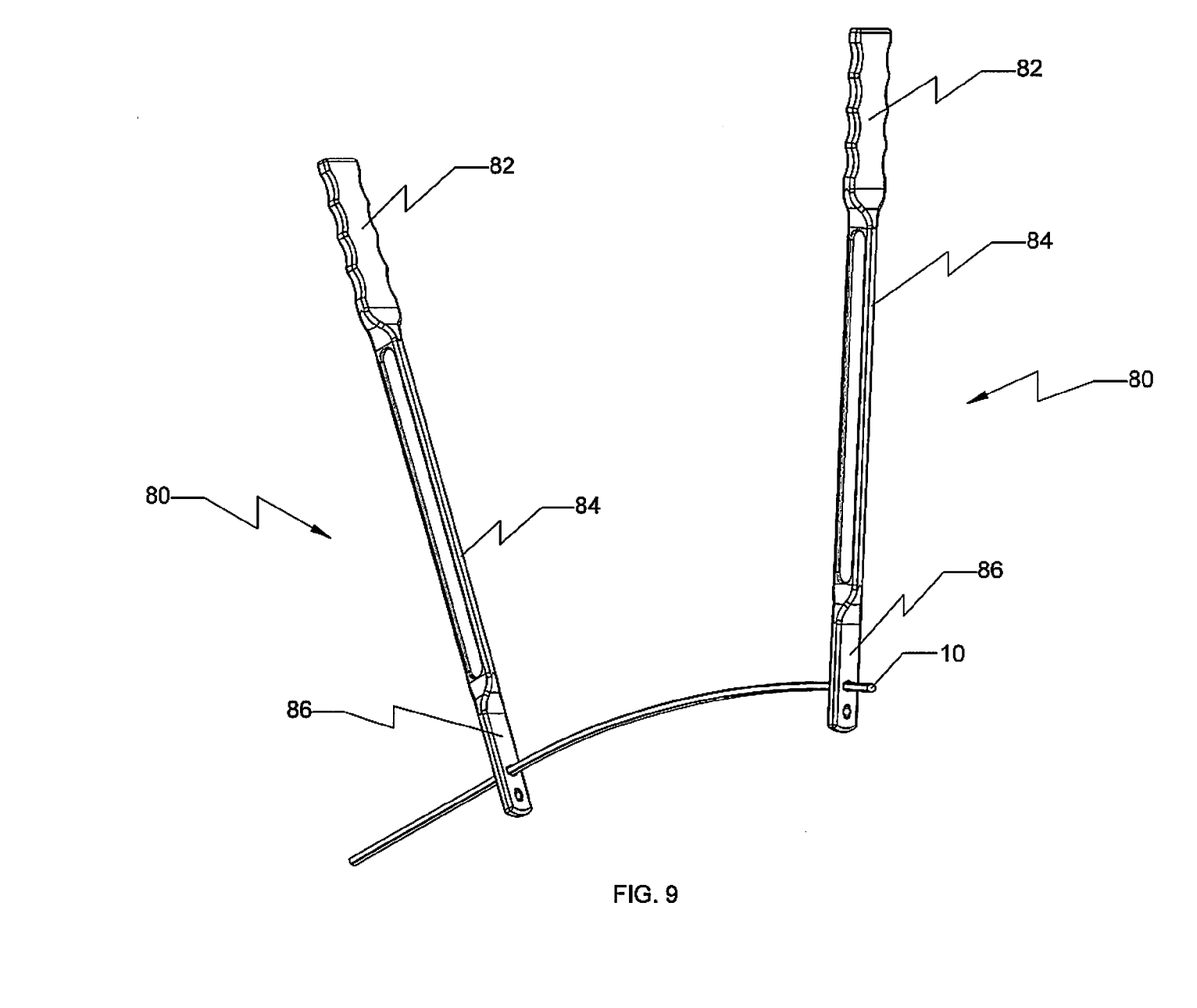
FIG. 9 is a perspective view of the pair of rod bender devices of FIG. 8 having the connecting rod of FIG. 3 inserted therethrough in a different orientation.

With particular reference to FIG. 7, each aperture 88 includes a pair of substantially rectangular walls 88a, 88b opposing each other and a pair of opposing connecting walls 88c that connect the pair of substantially rectangular walls 88a, 88b. The pair of substantially rectangular walls 88a, 88b is configured to engage the respective elongate rail portions 14a, 14b of connecting rod 10. In this manner, connecting rod 10 is inserted into each aperture 88 in a single orientation. Thus, in order to accommodate insertion of connecting rod in aperture 88 in various orientations, a plurality of apertures 88 are defined in engaging portion 86 in different orientations, as shown in FIGS. 8 and 9. For example, the pair of apertures 88 defined in engaging portion 86 is oriented at a 90-degree angle, whereby the rectangular portions of apertures 88 are orthogonal to each other. In this manner, the user can bend connecting rod 10 in both an anterior-posterior orientation and a medial-lateral orientation. It is also contemplated that connecting rod 10 may be inserted in non-corresponding apertures 88 in rod bender devices 80 to facilitate twisting of connecting rod 10, if necessary or desired.

The length of elongate body 84 may be tailored to meet the needs of the surgical application to provide a suitable long moment arm necessary to provide the user a mechanical advantage to bend connecting rod 10. In addition, it is also envisioned that elongate body 84 may be a hollow tubular member and/or define lightening holes to reduce the weight of device 80.

It is also envisioned that spinal stabilization system 100 may be used with other surgical instruments such as, e.g., a rod reduction device, configured to reduce a rod into position in a rod receiving slot in a head of a bone screw with a controlled, measured action. Reference may be made to U.S. Patent Application Publication Nos. 2009-0018593 and 2011-0087298, the entire contents of each of which are incorporated herein by reference, for a detailed discussion of the construction and operation of a rod reduction device.

In use, the user implants a plurality of bone screws 50 in vertebral bodies of a patient. Threaded shank 54 can be driven into the desired vertebral body by providing torsional force via a driving tool (not shown) configured to mate with and grip bone screw 50. After shank 54 is positioned within the vertebral body and the driving tool is removed from bone screw 50, connecting rod 10 is positioned within slot 53 of head portion 52.

In particular, spinal stabilization system 100 can be utilized to correct spinal deformity. Prior to securing connecting rod 10 with bone screw 50, the surgeon can manipulate and correct the curve of the spinal column, i.e., to manually manipulate and reduce the "rib hump." After placing the spine in proper position, the surgeon can bend connecting rod 10 prior to securing connecting rod 10 to the first two points of the spinal column where the construct is to be attached.

The surgeon can bend connecting rod 10 by utilizing the pair of rod bender devices 80. In use, connecting rod 10 is inserted through apertures 88 of rod bender devices 80 and force is applied at handle members 82 of rod bender devices 80 to appropriately contour and shape connecting rod 10 to a desired curve.

At this time, connecting rod 10 is positioned in respective slots 53 of bone screws 50 implanted in vertebral bodies. Set screws 60 can now be threadably inserted into head portion 52 of bone screw 50. Prior to fully securing connecting rod 10 to bone screws 50, the surgeon may once again utilize rod bender devices 80 to position connecting rod 10 to a desired orientation. As discussed hereinabove, slight gap 59 (FIG. 1) between wall 56 and elongate rail portions 14*a*, 14*b* of connecting rod 10 enables the surgeon to pivot connecting rod 10 about elongate rounded section 12 in slot 53 to position connecting rod 10 to a desired orientation. Upon positioning connecting rod 10 to a desired orientation, the surgeon can now secure connecting rod 10 with bone screws 50 by further tightening set screws 60. The rod and bone screw combination of the present disclosure may provide particular advantages in, e.g., scoliosis or other spinal deformity surgery, in which high stress levels are exerted upon such constructs at particular levels in the construct or over the entire length of such a construct.

Although the illustrative embodiments of the present disclosure have been described herein with reference to the accompanying drawings, the above description, disclosure, and figures should not be construed as limiting, but merely as exemplifications of particular embodiments. It is contemplated that the amount of gap 59 may be tailored to the procedure being performed. For example, the width of elongate rail portions 14*a*, 14*b* may be tailored to meet the needs of a particular surgical procedure that requires a particular degree of freedom to adjust orientation of connecting rod 10 in slot 53. One skilled in the art will recognize that the present disclosure is not limited to use in spine surgery, and that the instrument and methods can be adapted for use with any suitable surgical device. It is to be understood, therefore, that the disclosure is not limited to those precise embodiments, and that various other changes and modifications may be effected therein by one skilled in the art without departing from the scope or spirit of the disclosure.

What is claimed is:

1. A spinal stabilization system comprising:
a connecting rod including an elongate rounded section, a pair of elongate rail portions, and a pair of neck portions, each neck portion connecting the elongate rounded section with one of the elongate rail portions, each of the pair of elongate rail portions extending radially outward from the elongate rounded section and diametrically opposing the other one elongate rail portion of the pair of elongate rail portions, at least one elongate rail portion of the pair of elongate rail portions defining a planar surface; and
a bone screw including a head portion defining a slot, a shank extending longitudinally from the head portion, and a set screw configured to secure the connecting rod in the slot, the slot including a leading end portion configured to receive one elongate rail portion of the pair of elongate rail portions and a trailing end portion configured to engage the set screw, wherein the connecting rod is pivotable about the elongate rounded section in the slot.

2. The spinal stabilization system according to claim 1, at least one elongate rail portion of the pair of elongate rail portions includes a non-circular cross-section.

3. The spinal stabilization system according to claim 2, wherein the non-circular cross-section is rectangular.

4. The spinal stabilization system according to claim 1, wherein at least one elongate rail portion of the pair of elongate rail portions includes an arcuate surface.

5. The spinal stabilization system according to claim 4, wherein the arcuate surface of the at least one elongate rail portion of the pair of elongate rail portions conforms to a contour of the leading end portion of the slot defined in the bone screw.

6. The spinal stabilization system according to claim 1, wherein the planar surface of the at least one elongate rail portion of the pair of elongate rail portions is configured to be in a surface contact with the set screw.

7. The spinal stabilization system according to claim 1, wherein a width of at least one elongate rail portion of the pair of elongate rail portions is smaller than the diameter of the elongate rounded section.

8. The spinal stabilization system according to claim 1, wherein at least one neck portion of the pair of neck portions of the connecting rod is narrower than the elongate rounded section of the connecting rod.

9. The spinal stabilization system according to claim 8, wherein the at least one neck portion of the pair of neck portions includes a pair of concave sides joining the respective elongate rail portion with the elongate rounded section.

10. The spinal stabilization system according to claim 1, wherein the connecting rod is made of titanium or titanium alloy.

11. The spinal stabilization system according to claim 1, wherein the bone screw and the connecting rod are made of the same material.

12. The spinal stabilization system according to claim 1, wherein the connecting rod is monolithically formed.

13. The spinal stabilization system according to claim 1, wherein the elongate rounded section has a substantially circular cross-section.

14. A spinal stabilization system comprising:
a connecting rod including an elongate rounded section, a pair of elongate rail portions, and a pair of neck portions, each neck portion connecting the elongate rounded section with one of the elongate rail portions, each of the pair of elongate rail portions extending radially outward from the elongate rounded section and diametrically opposing the other one elongate rail portion of the pair of elongate rail portions, at least one neck portion of the pair of neck portions of the connecting rod is narrower than the elongate rounded section of the connecting rod, each of the pair of neck portions includes a pair of concave sides joining the respective elongate rail portion with the elongate rounded section; and
a bone screw including a head portion defining a slot, a shank extending longitudinally from the head portion, and a set screw configured to secure the connecting rod in the slot, the slot including a leading end portion configured to receive one elongate rail portion of the pair of elongate rail portions and a trailing end portion configured to engage the set screw, wherein the connecting rod is pivotable about the elongate rounded section in the slot.

15. A spinal stabilization system comprising:
a connecting rod including an elongate rounded section, first and second elongate rail portions diametrically opposing each other, and first and second neck portions connecting the elongate rounded section with the first and second elongate rail portions, respectively, the first and second elongate rail portions symmetrically arranged with respect to the elongate rounded section, at least one of the first or second elongate rail portions defining a width smaller than a width of the elongate rounded section; and a bone screw including a head portion defining a slot, a shank extending longitudinally from the head portion, and a set screw configured to secure the connecting rod in the slot, the slot including a leading end portion configured to receive one of the pair of elongate rail portions and a trailing end portion configured to engage the set screw, wherein the connecting rod is pivotable about the elongate rounded section in the slot.

16. The spinal stabilization system according to claim 15, wherein at least one of the first or second elongate rail portions includes a non-circular cross-section.

\* \* \* \* \*